US006384193B1

(12) United States Patent
Reed et al.

(10) Patent No.: US 6,384,193 B1
(45) Date of Patent: May 7, 2002

(54) AGENTS FOR THE REGULATION OF OESTROGEN SYNTHESIS

(75) Inventors: Michael John Reed; Anita Singh, both of London; Atul Purohit, Harrow, all of (GB)

(73) Assignee: Imperial College of Science Technology and Medicine, London (GB)

( * ) Notice: Subject to any disclaimer, the term of this patent is extended or adjusted under 35 U.S.C. 154(b) by 0 days.

(21) Appl. No.: 09/286,896

(22) Filed: Apr. 6, 1999

Related U.S. Application Data

(63) Continuation-in-part of application No. PCT/GB97/02780, filed on Oct. 9, 1997.

(30) Foreign Application Priority Data

Oct. 9, 1996 (GB) .............................................. 9621095

(51) Int. Cl.[7] .......................... C07A 14/00; C07A 5/00; G01N 33/566
(52) U.S. Cl. .................. 530/350; 530/326; 435/7.2
(58) Field of Search .............................. 530/326, 350; 435/7.2

(56) References Cited

U.S. PATENT DOCUMENTS 5,210,075 A  5/1993  Scholz et al. ................. 514/14

FOREIGN PATENT DOCUMENTS

WO  WO 95/11303  * 4/1995
WO  WO 96/17869  * 6/1996

OTHER PUBLICATIONS

Singh et al. IL–6sR: Release from MCF–7 breast cancer cells and role in regulating peripheral oestrogen synthesis. Journal of Endocrinology, vol. 147, pp. R9–R12, 1995.*

Singh et al., "Il–6sR: Release From MCF–7 Breast Cancer Cells and Role In Regulating Peripheral Oestrogen Synthesis", Journal of Endocrinology, vol. 147, 1995, pp. R9–R12.

Purohit et al., "Regulation of Aromatase and Sulphatase in Breast Tumor Cells", Journal of Endocrinology, vol. 150, Sep. 1996, pp. S65–S71.

Grube et al., "Identification of a Regulatory Domain of the Interleukin–6 Receptor", Journal of Biological Chemistry, vol. 269, No. 32, 1994, pp. 20791–20797.

Jordan, Scientific American, Oct. 1998, 279(4):60–67 ("Designer Estrogens"; "Drugs that Prevent Breast Cancer").

Thomas et al., Hum Reprod., 1994, 9(11):1991–6.

Singh et al., J. Reprod. Fertil., 1994, 100(2):367–74.

Ribot et al., Ann Endochrinol. (Paris), 1995, 56(6):603–8.

Jarvinen et al., Scand J. Immunol., 1996, 44(1):15–20.

* cited by examiner

*Primary Examiner*—Yvonne Eyler
*Assistant Examiner*—Joseph F. Murphy
(74) *Attorney, Agent, or Firm*—Frommer Lawrence & Haug LLP; Thomas J. Kowalski

(57) ABSTRACT

A system comprising a IL-6-IL-6sR complex and an agent that can block the interaction of the complex with gp130 to regulate oestrogen synthesis.

4 Claims, 2 Drawing Sheets

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<221> NAME/KEY: PEPTIDE
<222> LOCATION: (1)..(16)
<223> OTHER INFORMATION: sequence of a synthetic peptide corresponding -continued

```
         to the regulatory site residues 249-264 of interleukin-6
         receptor (IL-6R)

<400> SEQUENCE: 1

Tyr Arg Leu Arg Phe Glu Leu Arg Tyr Arg Ala Glu Arg Ser Lys Thr
1               5                   10                  15
```

AGENTS FOR THE REGULATION OF OESTROGEN SYNTHESIS

RELATED APPLICATIONS

This application is a continuation-in-part of PCT/GB97/02780, filed Oct. 9, 1997, designating the U.S., claiming priority from GB 9621095.0, filed Oct. 9, 1996; and, each of these documents, as well as all documents cited herein, and all documents referenced or cited in documents cited herein, are hereby incorporated herein by reference.

FIELD OF THE INVENTION

This invention relates to a system for regulating oestrogen synthesis, a method of regulating an oestrogen-producing enzyme, an assay for determining whether a compound is an agent capable of regulating oestrogen synthesis, a related kit, and the use of an agent in an oestrogen-dependent system.

BACKGROUND OF THE INVENTION

Oestrogens are the most potent mitogens known to stimulate the growth of breast tumours and in postmenopausal women most of the oestrogen required for tumour growth is formed in situ within the breast (Reed et al., 1989). Three main enzyme complexes are involved in oestrogen synthesis in breast tumours, i.e. aromatase, which converts androstenedione to oestrone; oestrone sulphatase (or E1-STS), which regulates the formation of oestrone from oestrone sulphate; and oestradiol dehydrogenase (or E2DH), which converts oestrone to the biologically active oestrogen, oestradiol.

In Singh et al.,(1995) we proposed that the interleukin-6 soluble receptor (or IL-6sR) may regulate the ability of IL-6 to stimulate oestrogen synthesis in breast cancer cells and breast tumours. Significant arbmatase activity was detectable in IL-6 stimulated fibroblasts derived from subcutaneous adipose tissue, but the combination of IL-6 sR plus IL-6 resulted in a marked 21-fold stimulation of aromatase activity. To examine the control of IL-6sR release, the effects of oestradiol, 4-hydroxytamoxifen (or 4-OHT), dexamethasone, TPA, TNFα, or IL-6 on this process was examined using MCF-7 breast cancer cells. Oestradiol, TNFα and dexamethasone all markedly increased IL-6sR release. While 4-OHT had a small stimulatory effect on IL-6sR release, it blocked the ability of oestradiol to increase IL-6sR release. Significant concentrations of IL-6sR were also detected in conditioned medium collected from lymphocytes and macrophages and in cytosols prepared from normal and malignant breast tissues. These results indicate that IL-6sR may have a role in potentiating the effect of IL-6 on oestrogen synthesis in breast cancer cells.

Cytokine, including IL-6, act by binding to membrane spanning receptors. For IL-6, the receptor (or IL-6R) complex consists of a 80 kDa (gp80) ligand binding sub-unit and a 130 kDa (gp130) signal transducing protein. The small gp80 sub-unit binds IL-6 with low affinity and must associate with the larger gp130 protein in order for high affinity binding and signal transduction to occur. A 55 kDa soluble form of gp80 (i.e. IL-6sR) is also found in serum, but unlike other known soluble cytokine receptors, which antagonise the effects of their respective cytokines, IL-6sR enhances the response to IL-6 in some biological systems. The IL-6sR is formed by limited proteolysis (shedding), but little is known about the factors which regulate this process (Mullberg et al., 1993).

Without wishing to be bound by any theory, we believe that a IL-6-IL-6sR complex is formed which has an important role in regulating at least aromatase activity. The development of a polypeptide which blocks the ability of the IL-6-IL-6sR complex to interact with gp130 provides a novel and surprising way of inhibiting the activity of this enzyme, and will thus influence oestrogen production and oestrogen-dependent systems.

Grube and Cochrane (1994) identified a 16 amino acid peptide, based upon part of the IL-6R external domain, but for a completely different application namely for blocked stimulation of B9 cell mitogenesis.

Reference is also made to U.S. Pat. No. 5,210,075, International Patent application No. WO 95/11303, Purohit et al., Regulation of Aromatase and Sulphatase in Breast Tumor Cells, Journal of Endocrinology, vol. 250, September 1996, pp S65–S71, and Grube et al., "Identification of a Regulatory Domain of the Interleukin-6 Receptor", Journal of Biological Chemistry, vol. 269, no. 32, 1994, pp. 20791–20797.

SUMMARY OF THE INVENTION

The present invention provides a system for regulating oestrogen synthesis, a method of regulating an oestrogen-producing enzyme, an assay for determining whether a compound is an agent capable of regulating oestrogen synthesis, a related, the use of an agent in an oestrogen-dependent system (e.g., a system that depends upon oestrogen), and other embodiments which are disclosed in or obvious from the following Detailed Description.

DETAILED DESCRIPTION

Thus according to one aspect of the present invention there is provided a system comprising a IL-6-IL-6sR complex and an agent that can block the interaction of the complex with gp130 to regulate oestrogen synthesis.

According to another aspect of the present invention there is provided a method of regulating an oestrogen-producing enzyme in a system comprising a member of the IL-6 superfamily, IL-6sR and gp130, the method comprising adding to the system an agent that can block the interaction of a IL-6-IL-6sR complex with gp130.

Preferred members of the IL-6 superfamily include IL-6, IL-11 and oncostatin M, with IL-6 being especially preferred. However, it will be appreciated that other members of the IL-6 superfamily, including those which may become available, may be useful in the present invention, given that members work by a similar mechanism to IL-6 itself.

For the avoidance of doubt we would mention that the terminology "IL-6-IL6sR" as used in connection with the present invention indicates a complex of IL-6sR with members of the IL-6 superfamily and not just with IL-6.

The present invention is specifically exemplified using aromatase activity. However, other oestrogen-producing enzymes, especially E2DH and E1-STS, are regulated by a similar mechanism and a skilled worker would expect these other enzymes to be regulated by the present invention.

The agent useful in the present invention and which blocks the interaction of a IL-6-IL-6sR complex with gp130 can be termed an "anti-oestrogen". These may include compounds which are known to have an effect on breast cancer, such as 4-hydroxytamoxifen (or 4-OHT), but which have previously been implicated in a different system, compounds which are newly identified as having an anti-oestrogen effect and completely new compounds. Such a compound with a newly identified effect is the polypeptide whose sequence is shown in Seq. ID No. 1 and which has been designated "Arohib". Novel compounds include variants, derivatives and fragments of Arohib which retain the ability to block the interaction of a IL-6-IL-6sR complex with gp130. The terms "variant", "derivative" or "fragment" include any substitution of, variation of, modification of, replacement of, deletion of or addition of one or more amino acids from or to the sequence providing the resultant polypeptide is capable of behaving as an agent in accordance with the present invention. It is expected that the useful compounds will be peptides or polypeptides, but this may not necessarily be the case.

The term "anti-oestrogen" is a term of art, and its use in this description can be in accordance with its use in the art (see, e.g., Thomas et al., Hum Reprod, 1994, 9(11):1991–6; Singh et al., J Reprod Fertil, 1994, 100(2):367–74; Ribot et al., Ann Endocrinol (Paris), 1995, 56(6):603–8; Jarvinen et al., Scand J Immunol, 1996, 44(1):15–20: Jordan, Scientific American, Oct. 1998, 279(4):60–67 ("Designer Estrogens"; "Drugs that Prevent Breast Cancer")).

As IL-6sR is produced in large amounts by malignant cells, the agent may preferentially inhibit breast oestrogen synthesis. This would be an advantage in long-term prevention of breast cancer, for example, preventing possible bone loss due to other types of inhibition.

Indeed, the present invention provides an assay for determining whether a compound is an agent capable of regulating oestrogen synthesis comprising adding the compound under test to a system comprising a member of the IL-6 superfamily, IL-6sR and gp130, and determining whether the compounds blocks the interaction of a IL-6-IL6sR complex with gp130, wherein if the compounds blocks the interaction, then the compound is an agent capable of regulating oestrogen synthesis.

The present invention also provides a kit which is particularly useful for carrying out the assay of the present invention, and which includes a member of the IL-6 superfamily, IL-6sR and gp130. The kit may typically consist of a microculture plate containing compounds under test. Each compound may be present in a minimum of three wells (for statistical evaluation). More replicates may be used depending on the number of compounds to be screened. It will be appreciated that the assay and kit of the present invention are susceptible to high through-put screening using robotics.

It will further be appreciated that combinatorial chemistry can be used to synthesize a series of related agents to identify more active agents, once an agent has been identified.

Whether a compound is blocking the interaction of the complex and gp130 can be measured in any convenient way, for example, by assessment of aromatase activity.

Yet further aspects of the present invention include an agent when screened by the assay of the present invention, particularly for use as a pharmaceutical or in a medicament for the treatment of an oestrogen-dependent system.

The present invention particularly provides the use of Arohib or a variant, derivative fragment thereof as a pharmaceutical or in a medicament for the treatment of an oestrogen-dependent system.

Whilst it may be possible for the agents of the present invention to be administered as the raw agent, it is preferable to present them as a pharmaceutical formulation. According to a further aspect, the present invention provides a pharmaceutical formulation comprising an agent together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof.

The formulations include those suitable for oral (particularly inhaled), parenteral (including subcutaneous, transdermal, intradermal, intramuscular and intravenous and rectal) administration although the most suitable route may depend upon for example the condition and disorder of the recipient. The formulations may conveniently be presented in unit dosage form and may be prepared by any of the methods well known in the art of pharmacy. All methods include the step of bringing into association an agent of the present invention as herein defined or a pharmacologically acceptable salt or solvate thereof ("active ingredient") with the carrier which constitutes one or more accessory ingredients.

Formulations of the present invention suitable for oral administration may be presented as discrete units such as capsules, sachets or tablets each containing a predetermined amount of the active ingredient; as a powder or granules, as a solution or a suspension in an aqueous liquid or a non-aqueous liquid; or as an oil-in-water liquid emulsion or a water-in-oil liquid emulsion. The active ingredient may also be presented as a bolus, electuary or paste. Formulations for inhalation may be presented in any of the ways known to be effective e.g. metered dose inhalers.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, water-for-injection, immediately prior to use. Extemporaneous injection solutions and suspensions may be prepared from sterile powders, granules and tablets of the kind previously described.

Preferred unit dosage formulations are those containing an effective dose, as herein below recited, or an appropriate fraction thereof, of the active ingredient.

The compounds of the invention may typically be administered orally or via injection at a dose of from 0.001 to 1 mg/kg per day.

The present invention will now be described by way of example.

This invention may be embodied in other forms or carried out in other ways. The present embodiment is therefore considered as illustrative and not restrictive.

EXAMPLES

Figure 1:
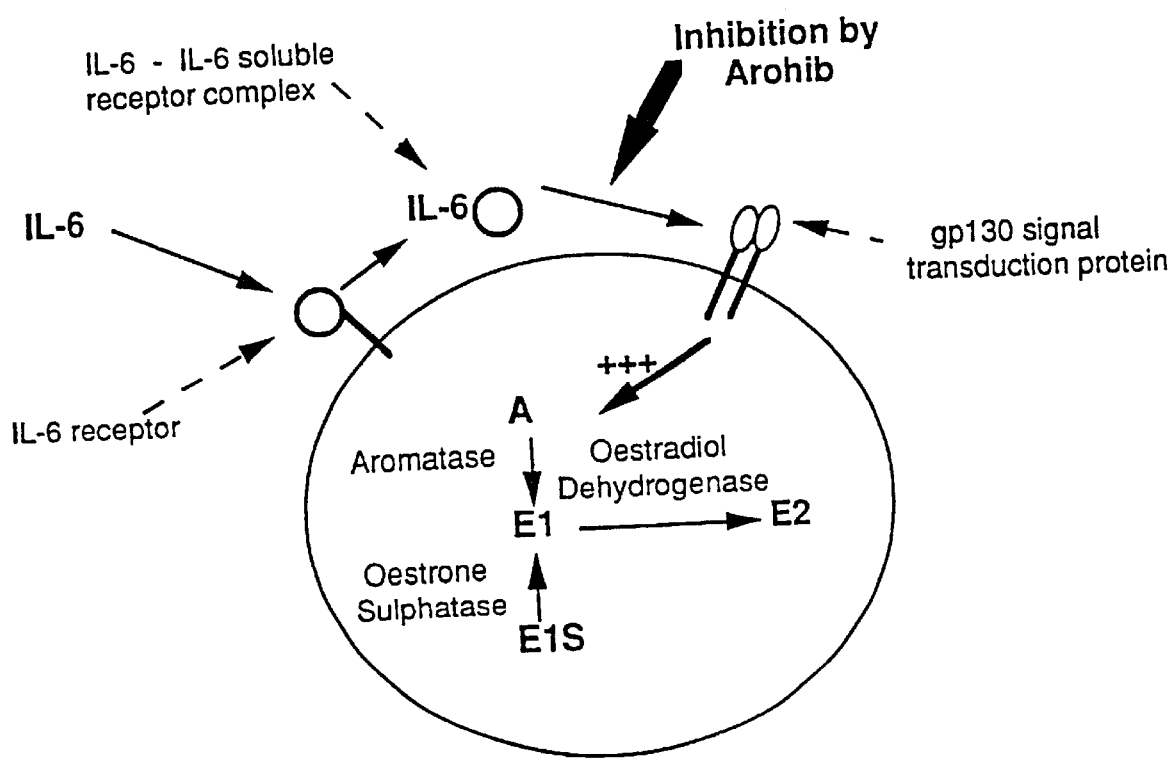
FIG. 1 is a schematic representation of the mechanism of IL-6 -IL-6 soluble receptor stimulation of oestrogen synthesis and inhibition by Arohib.

Example of Fibroblast Cell Culture and Aromatase Assay

Aromatase activity was assessed in primary cultures of stromal fibroblasts derived from sub-cutaneous adipose tissue. Cells were grown until 80% confluent when they were washed with Earle's balanced salt solution (5 ml) and cultured for 24 h in phenol red-free, serum-free Eagle's minimum essential medium. Experimental media were then added in the presence of dexamethasone (100 nmol/l), IL-6 (50 ng/ml, Bachem, Cambridge, U.K.), or IL-6 plus IL-6sR (250 ng/ml, R & D System Europe Ltd., Abingdon, U.K.) and incubated for a further 48 h.

Aromatase activity was assayed in intact fibroblast monolayers by measuring the production of hu $3H_2O$ from [1β-$^3$H] androstenedione (15–30 Ci/mmol, NEN-DuPont, Stevenage, U.K.) over a 20 h period (Newton et al., 1986). Aromatase activity measured under these conditions was linear with respect to time for up to 20 h (Macdiarmid et al., 1994). Cell number was determined by counting cell nuclei using a Coulter counter.

Example of MCF-7 Breast Cancer Cell Culture and Collection of Conditioned Medium MCF-7 cells were routinely cultured in minimum essential medium, Eagle modified with Earle's salts and Hepes buffer (20 mmol/l), 5% foetal calf serum and supplements. (Singh and Reed, 1991). When cells were 50–60% confluent they were washed with phosphate buffered saline (PBS) and treatments added in phenol red-free medium containing 5% stripped foetal calf serum and incubated for 48 h. The treatments were: oestradiol (1 nmol/l), 4-hydroxytamoxifen (4-OHT, 10 nmol/l), dexamethasone (100 nmol/l), 12-O-tetradecanoylphorbol-13-acetate (TPA, 100 nmol/l), TNFα (10 ng/ml, Bachem, Cambridge, U.K.) or IL-6 (10 ng/ml). At the end of this period, cells were washed with PBS and conditioned medium (CM) was collected by incubating the cells for a further 24 h in phenol red-free, serum-free medium. Duplicate flasks of cells were treated and CM was pooled before assaying IL-6sR concentrations.

Example of Collection of Conditioned Medium from Macrophages and Lymphocytes Blood (30 ml) was collected from a normal female subject and plasma containing white blood cells was obtained by the addition of 2% dextran in saline and centrifugation. After the addition of 0.83% ammonium chloride to remove contaminating red blood cells, the cells were pelleted by centrifugation, resuspended in phenol red-free minimum essential medium and transferred to a tissue culture flask. Cells were incubated at 37° C. for 4 h, during which time some cells (mainly macrophages) adhered to the flask, allowing separation from non-adherent (mainly lymphocytes) cells. CM was collected from lipopolysaccharide (10 μg/ml)—stimulated adherent and non-adherent cells over a 48 h period.

Example of Preparation of Cytosol from Normal and Malignant Breast Tissues

Cytosol from samples of normal or malignant breast tissue were prepared as previously described (Singh et al., 1989). Informed consent was obtained from the patient before collecting these tissues and the study was approved by the hospital ethics committee.

Example of ELISA Assay of IL-6sR

Concentration of IL-6sR in CM and cytosol were measured by a specific ELISA assay (R & D Systems Europe Ltd.,). Cross reaction of other cytokine receptors and cytokines in this assay is <0.001%. CM and cytosol exhibited parallelism with the IL-6sR standard curve when assayed at up to a 1:10 dilution. Intra- and inter- assay coefficients of variation were less than 10%.

Example

Peptide amino acid sequence also shown in Seq. ID No.1:
YRLRFELRYRAERSKT (This corresponds to peptide $^{249}Y$ 16 $T^{264}$ in the paper by Grube and Cochrane). We have designated this peptide "Arohib".

To examine the ability of Arohib to block the interaction of IL-6sR with gp130, fibroblasts were derived from normal breast tissue and cultured in growth medium containing fetal calf serum. When cells were 80% confluent, this medium was removed and replaced with serum-free medium. Cells were then treated as shown below with the results illustrated in FIG. 2.

| Controls | + | |
| IL-6 | + | 50 ng/ml |
| Arohib | + | 125 μM |
| IL-6 + | + | 50 ng/ml |
| IL-6sR | | 100 ng/ml |
| IL-6 + | + | 50 ng/ml |
| IL-6sR + | | 100 ng/ml |
| Arohib | | 125 μM |

Figure 2:
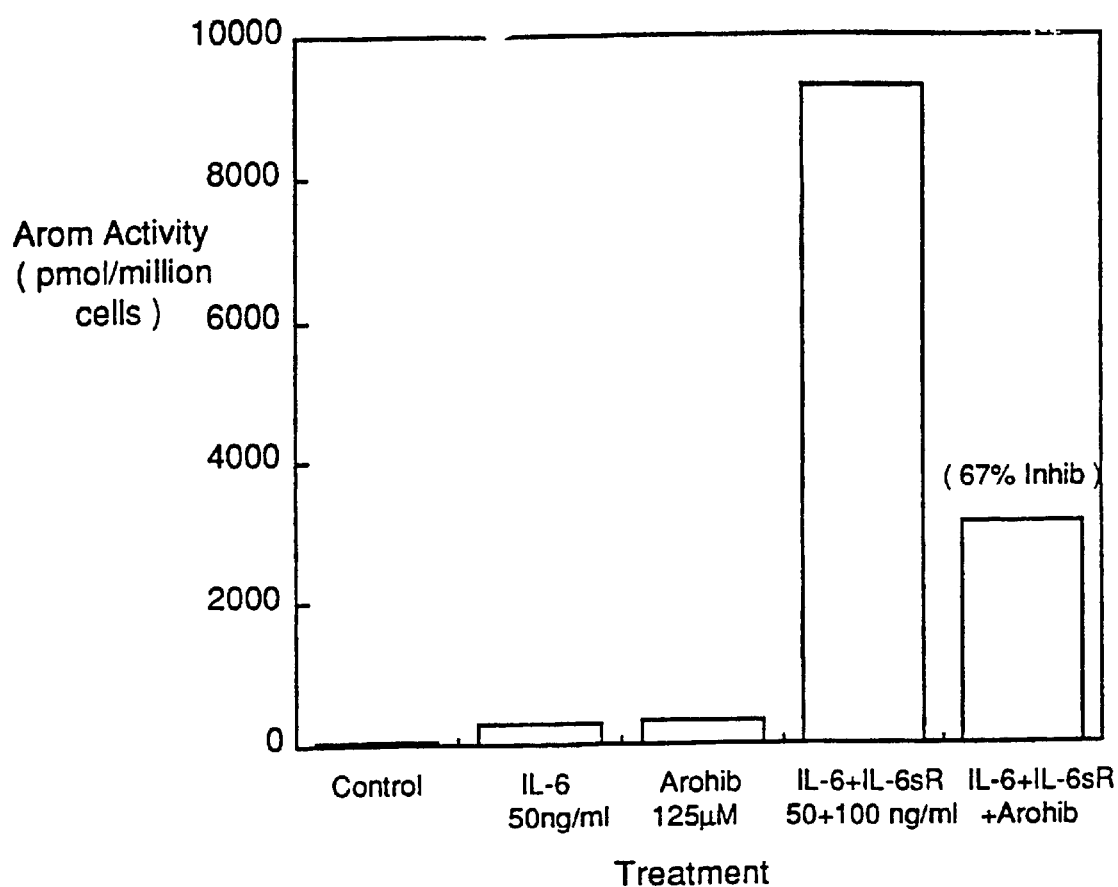
FIG. 2 is a graph showing the inhibition of IL-6 plus IL-6sR stimulated aromatase activity by Arohib.

As shown in FIG. 2, Arohib was added to cells 3 h prior to the addition of other treatments. The combination of IL-6 plus IL-6sR resulted in a 35-fold enhancement of aromatase activity compared with the increase from IL-6 alone. The addition of Arohib to the IL-6/IL-6sR complex resulted in a marked (67%) reduction in the ability of IL-6/IL-6sR to stimulate aromatase activity.

REFERENCES

Reed et al. (1989) Int. J. Cancer 44: 233–237

Singh et al (1995) J. Endocrinol. 147: R9–R12

Mullberg et al (1993) European J. Immunology 23: 473–480

Grube and Cochrane (1994) J. Biol. Chem. 264: 20791–20797

Macdiarmid et al. (1994) Molecular & Cellular Endrocinology 106; 17–21

Newton et al (1986) J. Steroid Biochemistry 24: 1033–1039

Singh and Reed (1991) J. Endrocrinol. 129: R5–R8

Singh et al (1989) Cancer Letters 44: 45–48

---

What is claimed is:

1. A system comprising all IL-6IL-6sR complex and an anti-oestrogen that can block the intraction of the complex with gp130 to regulate oestrogen synthesis.

2. The system according to claim 1, wherein the anti-oestrogen is 4-hydroxytamoxifen or a polypeptide having the sequence of SEQ ID NO: 1.

3. A system comprising an IL-6IL-6sR complex and a polypeptide having the sequence of SEQ ID NO: 1 that can block the interaction of the complex with gp130 to regulate oestrogen synthesis.

4. A system comprising an IL-6-IL-6sR complex and 4-hydroxytamoxifen that can block the interaction of the complex with gp130 to regulate oestrogen synthesis.

* * * * *

UNITED STATES PATENT AND TRADEMARK OFFICE
CERTIFICATE OF CORRECTION

PATENT NO.     : 6,384,193 B1
DATED          : May 7, 2002
INVENTOR(S)    : Michael John Reed et al.

It is certified that error appears in the above-identified patent and that said Letters Patent is hereby corrected as shown below:

<u>Title page,</u>
Item [73], Assigness, change "Imperial College of Science Technology and Medicine, London (GB)" to -- Sterix Limited, United Kingdom (GB) --

Signed and Sealed this

Sixteenth Day of March, 2004

JON W. DUDAS
*Acting Director of the United States Patent and Trademark Office*